United States Patent [19]

Kitaoka et al.

[11] Patent Number: 5,139,332

[45] Date of Patent: Aug. 18, 1992

[54] OPTICAL EMISSION SPECTROCHEMICAL STANDARD FOR METALS AND ALLOYS

[75] Inventors: Sanji Kitaoka; Susumu Nawata; Hisashi Hori; Katsumi Takahashi, all of Kanbara, Japan

[73] Assignee: Nikkei Techno-Research Co. Ltd., Tokyo, Japan

[21] Appl. No.: 591,938

[22] Filed: Oct. 2, 1990

[51] Int. Cl.$^5$ .................... G01N 21/71; G01N 21/66
[52] U.S. Cl. ..................... 356/243; 356/313
[58] Field of Search ............... 356/243, 313, 314

[56] References Cited

U.S. PATENT DOCUMENTS 3,877,811  4/1975  Mentrier et al. ............ 356/243 X

OTHER PUBLICATIONS

Ordelman et al. "A general method for quantitative spectrochemical analysis with the d.c. arc performed with solid samples in briquetted form" Spectrochimica Acta, 1966 vol. 22, pp. 313–321.

Van Nostrand's Scientific Encyclopedia, copyright 1976, p. 1823 Definition of "Powder Metallurgy".

*Primary Examiner*—Vincent P. McGraw
*Attorney, Agent, or Firm*—William J. Daniel

[57] ABSTRACT

A standard test specimen for optical emission spectrochemical analysis is prepared by molding into the specimen body finely divided particles consisting essentially of the metal or metal alloy to be analyzed without melting the same and preferably by plastic deformation of such particles. The resultant specimen is homogeneous throughout and stable in quality so that accurate analysis of any of its elements is possible and the suitability of the test material for a given product can be accurately predicted.

6 Claims, 4 Drawing Sheets

OPTICAL EMISSION SPECTROCHEMICAL STANDARD FOR METALS AND ALLOYS

BACKGROUND OF THE INVENTION

1. Field of the Invention

The present invention concerns a standard test specimen for optical emission spectrochemical analysis of metals and alloys which has a homogeneous content of metallic elements and of stable quality.

2. Description of the Prior Art

As a method capable of rapidly analyzing compositions of metals, optical emission spectrometry has been adopted for the analysis of various kinds of alloys in which the content of an element in a test sample to be analyzed is determined in accordance with a calibration curve showing the correlation between the spectral intensity ratio (absolute radiation power of an element / absolute radiation power of the base metal) and the concentration of the element in the standard sample.

In optical emission spectrometry, since the spectral intensity ratio of a sample to be analyzed is incorporated into a previously prepared calibration curve and the content of the element in the sample is determined from this curve, the precision of the analysis for the sample and its accuracy depends on the accuracy of the previously prepared calibration curve and the accuracy of the daily drift correction in the calibration curve (fluctuation of the spectral intensity ratio caused by the analyzing device). Accordingly, a standard sample of homogeneous and known element content is necessary for an accurate analysis.

By the way, as the standard sample used for such optical emission spectrometry, a disc-likeingot of 40 to 60 mm diameter×5 to 10 mm thickness prepared by casting a molten metal into a die is used as a standard sample after determining a standard composition value thereof by chemical analysis. Upon optical emission spectrometry, the surface of this standard sample is machined into a smooth surface and then a calibration curve is drawn based on the spectral intensity ratio caused by sparking predetermined positions in the surface. However, segregation often occurs upon solidification of the molten metal, as is usual, if a large amount of alloying elements are present. As a result, the spectral intensity varies depending on changes in the 2- or 3-dimensional positions of the surface to be sparked and, accordingly, accurate analysis is impossible with such a standard sample. In view of the above, for reducing the segregation upon solidification of the molten metal, the molten metal may sometimes be cast into an ingot rod of a small diameter by semi-continuous casting and then cutting into a disc-like shape.

However, segregation can not be overcome even if cast into an ingot rod of a small diameter and, in particular, segregation becomes more serious as the content of the element is increased. For instance, for Al-Si series alloys containing Si exceeding an eutectic point, primary Si crystals are precipitated and the segregation of such precipitated primary Si crystals makes the calibration curve and the drift correction therefor inaccurate even if it is cast into an ingot rod, making accurate analysis for the sample to be analyzed impossible.

OBJECT OF THE INVENTION

It is, accordingly, an object of the present invention to overcome the foregoing problems and to provide an optical emission spectrochemical standard for metals and alloys suitable for the preparation of an accurate calibration curve and conducting accurate drift correction.

SUMMARY OF THE INVENTION

The present inventors have made various studies for overcoming the foregoing problems and, as a result, have found that an optical emission spectrochemical standard for metals and alloys prepared from finely divided metal particles by mixing and molding can reduce the effect of the segregation of alloying elements and thus minimize errors in the analysis so as to make possible an accurate calibration curve and conduct accurate drift correction and, as a result, the content for each of the elements in the sample can be analyzed accurately.

That is, the foregoing object of the present invention can be attained by an optical emission spectrochemical standard for metals and alloys, especially aluminium and its alloys comprising a molding mixture of finely divided metal particles.

The metal particles may be prepared by a usual method but it is more effective when it is prepared by rapid solidification for the reasons to be described later.

Further, the molding mixture may be formed by means of a usual molding method but it is more effective when it is prepared by plastic deformation for the reasons to be described later.

The finely divided metal particles in the present invention means fine powder, grains, tiny pieces, foil, rod, fine wire, etc. Since the standard sample constituted as described above from such metal particles contains many such metal particles at the surface for analysis and they are randomly mixed together, if there is any segregation between the metal particles, they are averaged as a whole in the analyzing surface and can be formed as a homogeneous standard sample with less segregation due to 3-dimensional positions. Accordingly, an accurate calibration curve can be prepared upon optical emission spectrometry, an accurate drift correction is possible and, as a result, the content of elements in the sample can be analyzed accurately.

Further, if the metal particles are prepared as rapid solidification products, since they less subject to less segregation in themselves, a standard sample prepared by mixing and molding makes possible a more accurate calibration curve and accurate drift correction, and thus more accurate analysis of the content of the element in the sample to be analyzed.

Further, if the molding mixture of the metal particles is molded by plastic deformation, since any segregated regions among the metal particles are dispersed during plastic deformation such a standard sample can provide more acurate calibration curve and more accurate drift correction and, accordingly, the content of the element in the sample can be analyzed more accurately.

DESCRIPTION OF THE PREFERRED EMBODIMENT OF THE INVENTION

Figure 1:
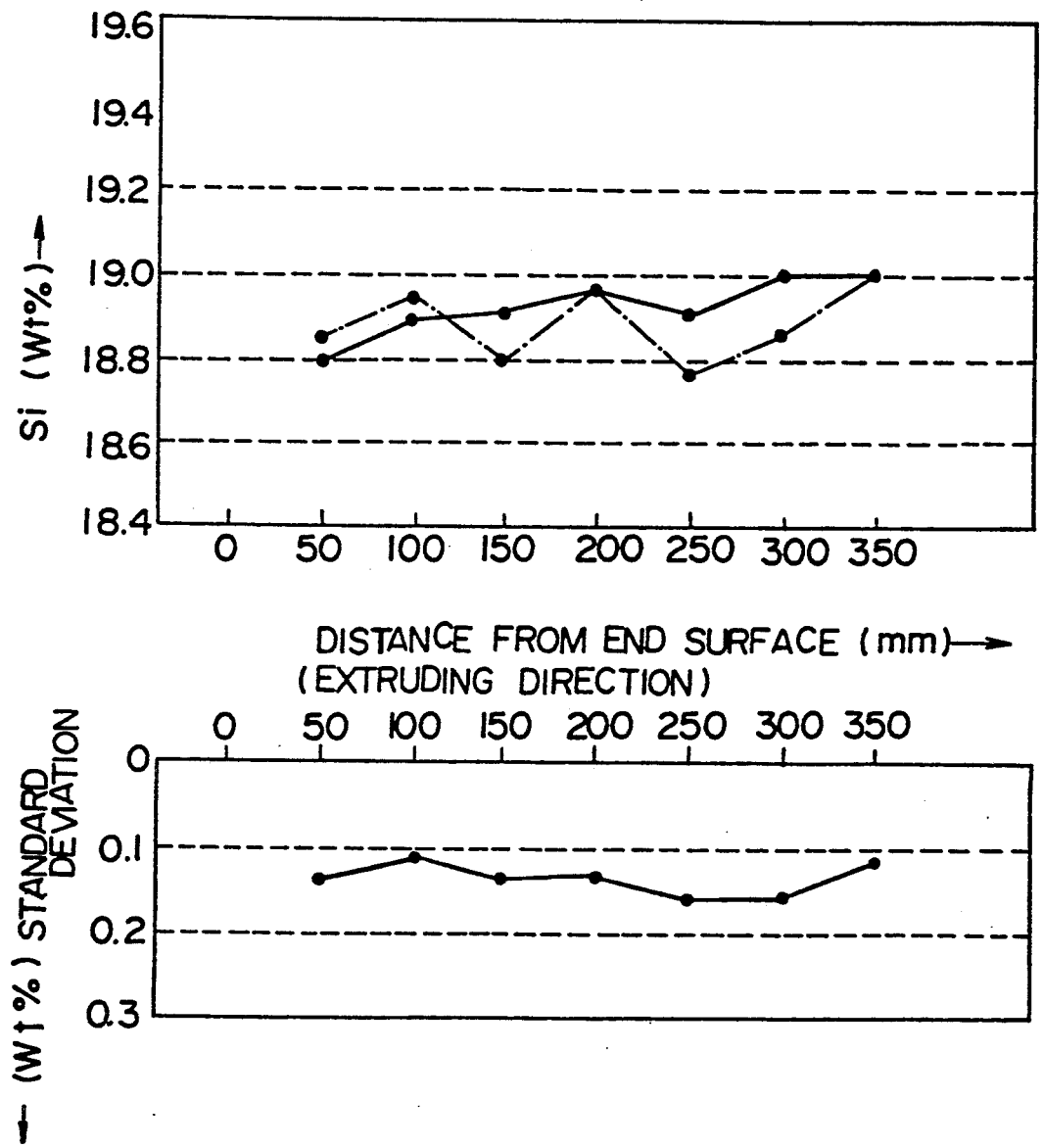

Description will now be made of the method of preparing a standard sample in the present invention.

Suitable metal particles can be obtained from a cast ingot prepared by casting a molten metal into a die, indirectly cooling the molten metal with water or directly chilling it, and then finely pulverizing the cast ingot physically as in a pulverizer, or by rolling it into a foil, rod or fine wire, followed by cutting. In addition, the metal particles can also be prepared by chemical reaction.

Mixing may be conducted in any usual mixer and it is most convenient, for the handling purposes, to mix and mold a single kind of metal particles with a selected composition. Alternatively, it is also possible to carry out mixing and molding while combining metal particles of different forms such as powder and fine wire. Further, not only the metal body of an identical composition but also the metal bodies of different compositions may be mixed and molded. For instance, for of preparing a standard sample of an Al-Si-Cu-Mg series alloy, a powder of an Al-Cu-Mg series alloy and a powder of a pure metal such as metallic silicon are mixed and molded, or powder for each of alloys of Al-Si, Al-Cu and Al-Mg are mixed and molded, or powders of the respective pure metals may be mixed and molded with each other. The combination is not restricted only to those as described above, but the shape of the metal particles, preparation method thereof, composition and the molding method can optionally be selected in the present invention.

Further, such metal particles can be molded, for example, by means of extrusion, rolling, forging and sintering.

Preparation of the metal particles prepared from the rapidly solidified cast ingot is particularly preferred since there is less segregation in the cast ingot. Further, fine powder prepared by rapid solidification of metal particles by means of an atomizing process, a method using a rotating perforated crucible, etc., or extremely fine wire or thin foil obtained by rapidly solidifying by means of single roll or twin-roll method or melt spinning process are more preferred since the casting product per se is fine and there is less segregation. In addition, since a molten metal at a relatively high temperature can be cast by the rapid solidification process, scattering of the contents in the cast products between the early stage and the later stage of the casting can be reduced and a cooling rate as high as $10^3°-10^{6°}$ C./sec can be obtained. Accordingly, there occurs less segregation within the interior of the metal particles upon solidification and a standard sample with minimum segregation and of stable quality can be obtained by preparing the molding product using the metal particles taken at any state. The solid test speciment can be molded, as described above, by pressing, extrusion, rolling, forging, etc. Among the methods of accomplishing the plastic deformation upon molding of the metal particles, extrusion fabrication is particularly preferred as a plastic deformation since a surface perpendicular to the flow of the metal during molding, that is, a cross section perpendicular to the extruding direction can be selected as the test surface for the optical emission spectrometry. Since the thickness of the original metal particles is reduced in accordance with the extrusion ratio the cross section in perpendicular to the extruding direction in this extrusion fabrication, this can provide a result equivalent to increasing the number of metal particles per unit cross sectional area were increased, making it possible to prepare a more accurate calibration curve and more accurate analysis for the composition of the sample. Since it is preferred that the number of metal bodies present per unit erea of the test surface for analysis be increased in order to improve the homogeneity of the molding product, metal particles having a cross sectional area as small as possible should be chosen. Take for illustration purposes, the size of the metal particles for the case of extrusion molding a metal powder into a round rod, cutting the rod perpendicular to the extruding direction to form a disc-like standard sample and using the cross section of the sample for the optical emission spectrometry. Assuming the diameter of the metal powder is r, the extrusion ratio is R and the diameter of the effective optical emission spectrometry test area is 5 mm, the number n of the powder particles present at the surface of the optical emission spectrometry test area can generally be expressed by the following equation:

$$n=(5/r)^2 \cdot R$$

Assuming the extrusion ratio as: R=5, n=125 when r=1 mm in the equation. This is equivalent to taking an average among 125 separate samples if there is any deviation in the composition between individual powder particles and, accordingly, stable analysis value is assured. In view of the above, the size of the metal particles of the molding product before plastic deformation is preferably less than 1 mm for the diameter in the case of powder, grains, etc. However, if it is less than 60 μm, further improvement can not be obtained and handling becomes rather difficult in view of the explosion danger. In the case of a piece, foil, etc. the thickness is less than 0.3 mm and, preferably, less than 0.1 mm. In the case of a rod, fine wire, etc. the outer diameter is less than 1 mm and, preferably, less than 0.5 mm. A metal particles of a size even greater by more than 4 to 5 times of the above-mentioned size can provide the same excellent effect as that obtained by using fine metal particles, by selecting a large plastic deformation ratio.

In view of the above, extrusion fabrication is particularly advantageous when the metal particles are grains, powder, wire, rod, foil, etc. for the reasons as described above. Further, the metal particles may be molded with plastic deformation by means of rolling, forging, etc. in addition to the extrusion. In this case, since it is generally necessary for the test sample to have a sufficiently large diameter as to at least enable analysis to be made a plurality of times within a sufficient area of the same surface, that is, a diameter of about 40 to 60 mm, in order to generate a surface of sufficient size perpendicular to the flow of the metal, a large scale fabrication is needed. Accordingly, analysis is usually conducted in practice on a surface parallel with the metal flow. In such a surface, since the metal particles comprises an elongated film, the number of the original metal particles per unit area is decreased as compared with that in the case of the extrusion fabrication and the homogenity of the sample is somewhat deteriorated. However, if metal particles of a small size is selected, a sample much more homogeneous than the conventional disc-like sample prepared by die casting or semicontinuous direct chill casting can be obtained.

In the present invention, the composition of the metal particles has no particular restriction. For instance, in the case of aluminum alloys, the present invention can provide particularly excellent results for an alloy containing such elements as Ti or Fe, etc. which are liable to be segregated upon solidification of the aluminum alloy exceeding the peritectic point or eutectic point, or Al-12 to 25 wt % Si series alloys containing Si which is liable to precipitate primary Si crystals exceeding the eutectic point. The present invention of course can provide an excellent effect also for aluminum alloys containing less than 12 wt % of Si as well. In addition, the present invention can also provide an excellent effect for aluminium alloys containing Pb, Bi, etc. which are liable to cause gravity segregation, Al-Ti-B series alloys which are liable to cause coagulation of intermetallic compounds, as well as Al-Cu-MG series alloys or Al-Cu-Mg-Zn series alloys containing Cu, Zn, Mg, etc.

If optical emission spectrometry using a standard sample according to the present invention is to be carried out with a test sample having a different metallurgical hysteresis from that of the conventional standard sample, since the spectral intensity ratio of Si is different even for an identical Si content depending presumably on the size of primary Si crystals, it is necessary to previously recognize the extent of that effect by preliminary measurement and to apply an appropriate correction (JIS/H1305).

DESCRIPTION OF THE ACCOMPANYING DRAWINGS

Figure 2A:
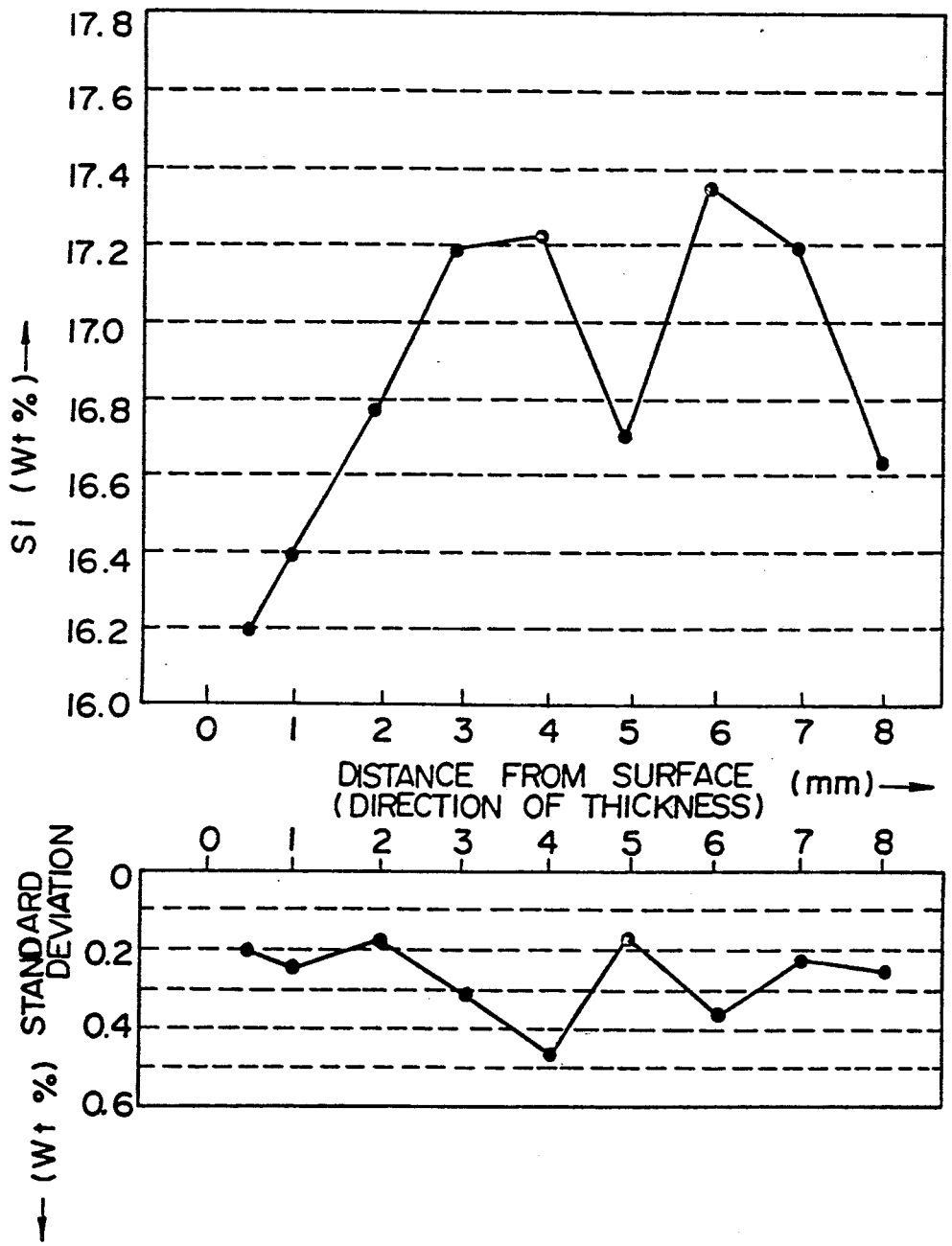
Figure 3:
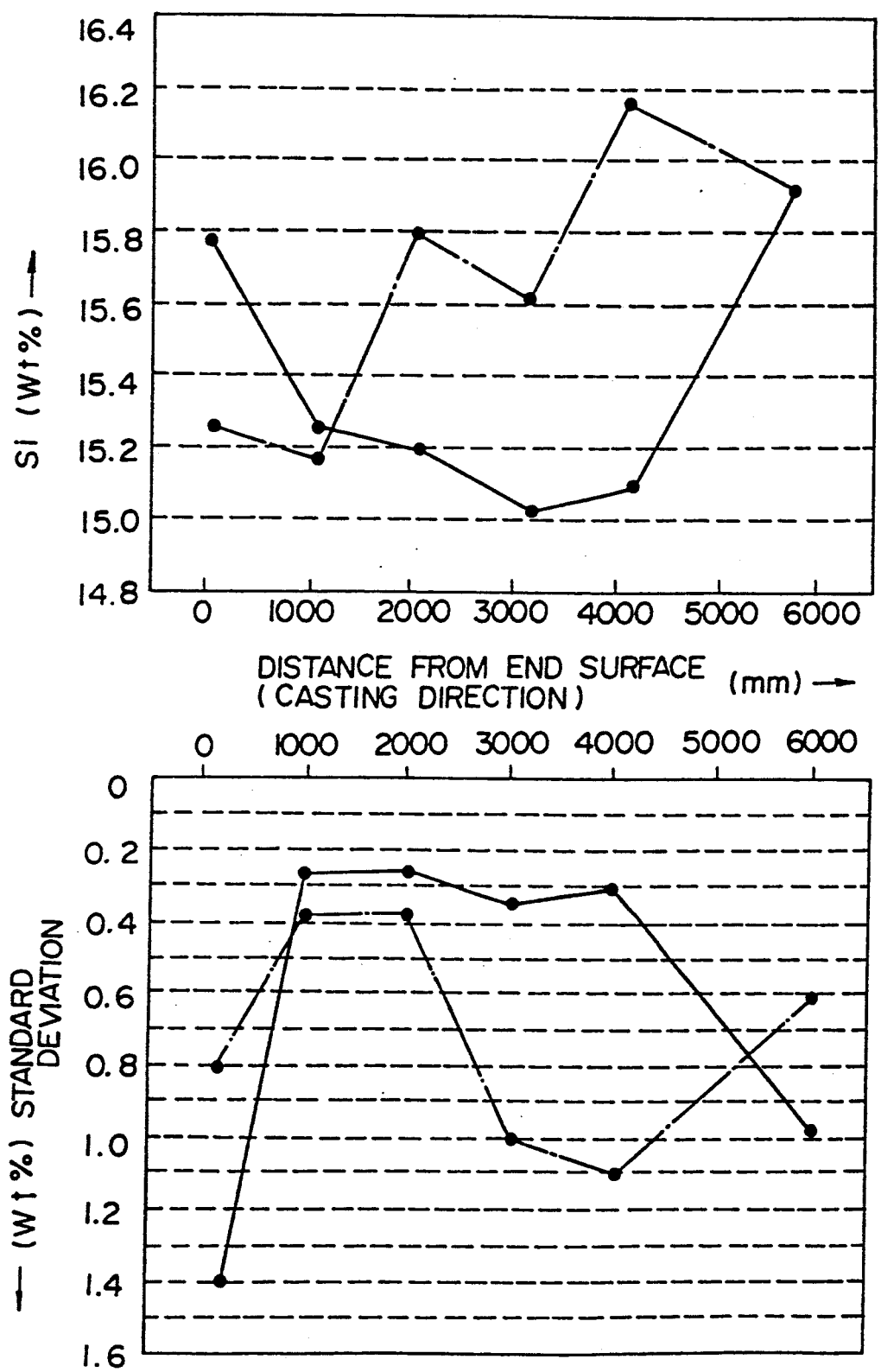

These and other objects, as well as advantageous features of the present invention will now be described more in detail with reference to examples of the invention in conjunction with the accompanying drawings, wherein FIG. 1 is a graph showing the analysis value and the standard deviation when the standard sample according to a present invention is subjected to optical emission spectrometry;

FIGS. 2A and B are graphs showing the analysis value and standard deviation when the samples prepared by a die casting method as in the prior art are subjected to optical emission spectrometry; and FIG. 3 is a graph showing the analysis value and the standard deviation for a cast rod cast by a horizontal semi-continuous casting method as in the prior art is subjected to optical emission spectrometry.

EXAMPLE

Example 1

JIS AC9B alloy (comprising a composition: Al—18.9 wt % Si—1.4 wt % Cu—10 wt % Mg—1.2 wt % Ni—0.4 wt % Fe) (calculated blending value) was prepared by melting at 850° C. and sprayed by rotating a perforated crucible to prepare granular metal particles with an average grain size of 0.8 mm (grain size from 0.3 to 3 mm) at a cooling rate of $10^2$-$10^3$° C./s. The metal particles were charged in a bottomed can having 100 mm inner diameter and 150 mm length and the can was extruded into a round rod of 40 mm diameter. The extruded round rod was cut in 50 mm lengths and a cut surface in perpendicular to the extruding direction was machined to prepare test specimens for optical emission spectrometry.

The optical emission spectrometry was conducted under the following conditions.
Emission source: high voltage spark method
Atmosphere: air
Counter electrode: graphite rod
Wavelength: Si 390.55 nm; Al 256.80 nm (internal standard line)
Element: Si
Spark position: central area (within ½ radius) and outer peripheral region (equivalent positions outside of ½ radius) in the surface perpendicular to the extruding direction on every 50 mm length.

Analysis for one specimen was conducted five times an identical surface.

Results of the analysis are shown in FIG. 1.

In FIG. 1, each of points represents an average value for five times of analysis. Further, the value for the standard deviation $\sigma_{n-1}$ for the times of measurement each by five times for the central area and the outer peripheral region, 10 times in total, for each of the specimens was from 0.11 to 0.16 wt %.

From the results of FIG. 1, the analysis value was between 18.7–19.0 wt %, the deviation for the analysis value depending on changes in the spark positions in the extruding direction is small irrespective of the high Si content and, in addition, the variation in the value for the standard deviation $\sigma_{n-1}$ for the identical surface is small being from 0.11 to 0.16 wt % and, accordingly, it can be seen that segregation depending on the test position is small and the specimens are suitable as an optical emission spectrochemical standard for hyper-eutectic Al-Si.

Example 2

The granular metal particles prepared in Example 1 were pressed by a 600 t press to obtain a pressed rod of 40 mm diameter × 100 mm length. The pressed rod was cut in 50 mm lengths and the surface in perpendicular to the longitudinal direction was finished to prepare a specimen for optical emission spectrometry. The optical emission spectrometry followed the same procedures as in Example 1. As the result of the analysis, the average value for the five points in the central area was 18.8 wt %, the average value for the five points in the outer peripheral regions was 19.0 wt % and the value for the standard deviation $\sigma_{n-1}$ for the 10 spark points was 0.19 wt %. From the result, since the deviation of the analysis value is small and, in addition, the variation of the value for the standard deviation $\sigma_{n-1}$ for the identical surface is small, it can be seen that the segregation depending on the test position is small and the specimen is suitable as an optical emission spectrochemical standard for hyper-eutectic Al-Si alloys.

Comparative Example 1

Figure 2B:
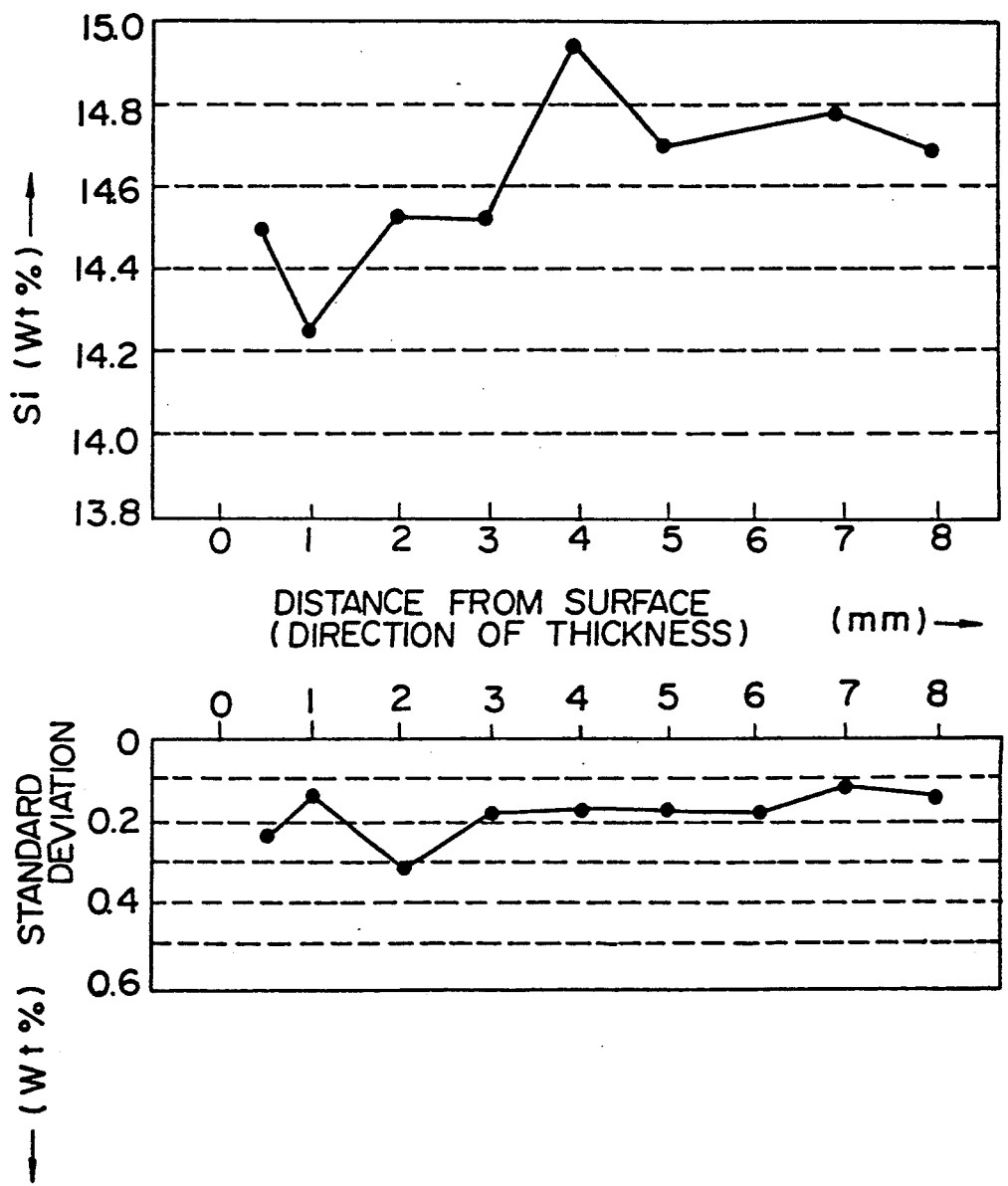

As a comparison, high Si alloy (Al 16.5 wt % Si—4.7 wt % Cu—0.55 wt % Mg—0.3 wt % Fe) and low Si alloy (Al 14.6 wt % Si—0.46 wt % Cu—0.5 wt % Mg—0.3 wt % Fe) (calculated blending value) were prepared by melting at 800° C. as alloys corresponding to AA Standard (Aluminum Association) A 390.0 and they were cast each into a die having a disc-like cavity with 55 mm diameter and 10 mm thickness, to obtain die cast specimens. Each die cast specimen was machined at the surface perpendicular to the central axis and subjected to the optical emission spectrometry. The spark position was set to the outer circumferential region of the surface perpendicular to the central axis. Analysis for one specimen was conducted by measurement five times on the same surface and then such measurements were repeated after cutting the specimen each by 1 mm. The results of the analysis are shown in FIGS. 2A and B. Each of the points in FIG. 2 is an average value for the five measurements described above.

The observed value for the high Si alloy shown in FIG. 2A was between 16.2 to 17.4 wt % and, since segregation is large along the direction of the thickness and the value for the standard deviation $\sigma_{n-1}$ (n=5) for the identical surface is as great at from 0.18 to 0.47 wt %, it can be seen that the segregation depending on test position is large and the specimen is not suitable as the standard sample. Further, the analysis value for the low Si alloy shown in FIG. 2B was between 14.2 and 15.0 wt % and, since the segregation along the direction of the thickness is large and the standard deviation $\sigma_{n-1}$ (n=5) for the identical surface is as large as from 0.12 to 0.31 wt %, it can be seen that segregation is large depending on the test positions and the specimen is not suitable as the standard sample.

Comparative Example 2

As a comparison, AA Standard A 390.9 alloy (Al—15.5 wt % Si—4.7 wt % Cu—0.55 wt % Mg—0.3 wt % Fe) (calculated blending value) was prepared by melting at 750° C. and a cast rod of 58 mm diameter was obtained by semi-continuous casting. The sparking position for the cast rod was set to the central area (within ½ radius) and the outer peripheral region thereof (equivalent positions outside of ½ diameter) the surface in perpendicular to the casting direction and cut on every 1000 mm in the longitudinal direction. Analysis for one specimen was conducted five times for each of the central area and the outer peripheral region for one identical surface. The results of the analysis are shown in FIG. 3.

In FIG. 3, each of points is an average value for five measurements. Further, the value for the standard deviation $\sigma_{n-1}$ (n=10) for a total of 10 measurements, that is, each five times for each of the central area and the outer peripheral region for each of the specimens was from 0.5 to 1.0 wt %.

From the results of FIG. 3, the analysis value was between from 15.0 to 16.2 wt %, the segregation of the analytical value depending on the spark positions in the casting direction is large and the standard deviation $\sigma_{n-1}$ (n=10) within the identical surface was as large as from 0.5 to 1.0 wt % and it can be seen that the body is not suitable as the standard sample.

As has been described above, since the content of metallic elements is homogeneous and quality is stable in the present optical emission spectrochemical standard specimens for metals and alloys, especially aluminium and its alloys according to the present invention, the amount of an element present in the sample to be analyzed can be accurately analyzed and determined and, accordingly, the exact performance of such metals and alloys for various kinds of products or semi-products can be forecast and recognized accurately.

What is claimed is:

1. A standard test specimen for optical emission spectrochemical analysis which consists essentially of finely divided particles of a metal or metal alloy molded without melting into a test body and having at least one flat surface which can be subjected to such analysis.

2. The test specimen of claim 1 which consists essentially of an aluminum alloy.

3. The test specimen of claim 2 wherein said alloy contains 12-25% by wt of Si.

4. The test specimen of claim 1 wherein said finely divided particles are obtained by rapid solidification from a molten condition.

5. The test specimen of claim 1 wherein said particles are molded by plastic deformation.

6. A method of making a standard test specimen for optical emission spectrochemical analysis which comprises subjecting finely divided particles consisting essentially of an aluminum alloy to plastic deformation below the melting temperature of such alloy to shape the same into a specimen body and providing at least one flat surface on said body for said analysis.

* * * * *